(12) United States Patent
Crabtree, Jr. et al.

(10) Patent No.: US 9,693,868 B2
(45) Date of Patent: *Jul. 4, 2017

(54) HINGED JOINT SYSTEM

(71) Applicant: Smith & Nephew, Inc., Memphis, TN (US)

(72) Inventors: Paul Charles Crabtree, Jr., Nesbit, MS (US); Greg Marik, Germantown, TN (US); Abraham Biglari Salehi, Bartlett, TN (US); Kevin Weaver, Bartlett, TN (US); Frantz Langlais, Rennes (FR); Denis Huten, Vincennes (FR); Dennis Harrison, Nesbit, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/185,701

(22) Filed: Jun. 17, 2016

(65) Prior Publication Data

US 2016/0287399 A1    Oct. 6, 2016

Related U.S. Application Data

(63) Continuation of application No. 14/714,568, filed on May 18, 2015, now Pat. No. 9,381,087, which is a
(Continued)

(51) Int. Cl.
*A61F 2/38* (2006.01)
*A61B 17/16* (2006.01)
(Continued)

(52) U.S. Cl.
CPC ........ *A61F 2/3845* (2013.01); *A61F 2/30744* (2013.01); *A61F 2/385* (2013.01);
(Continued)

(58) Field of Classification Search
CPC ...... A61F 2/384; A61F 2/3845; A61F 2/3854; A61F 2/3868; A61F 2/389; A61F 2/385; A61F 2/3859
See application file for complete search history.

(56) References Cited

U.S. PATENT DOCUMENTS 3,765,033 A * 10/1973 Goldberg ............... A61F 2/384
623/20.26
3,824,630 A    7/1974 Johnston
(Continued)

FOREIGN PATENT DOCUMENTS

DE    3022668    12/1981
DE    4102509    6/1996
(Continued)

OTHER PUBLICATIONS

Brochure entitled Aesculap EnduRo Gekoppelte Knieendoprothese Aesculap Orthopaedics B/Braun Sharing Expertise, 8 pages, known prior to Jul. 16, 2010.
(Continued)

*Primary Examiner* — Anu Ramana
(74) *Attorney, Agent, or Firm* — Fish & Richardson P.C.

(57) ABSTRACT

Methods, systems, and devices for replacement of a joint with a prosthetic system that replicates the natural kinematics of the joint is disclosed. A prosthetic system according to one embodiment includes a tibial component having a tibial plateau and a tibial stem portion, the tibial plateau having a top side and a bottom side, a tibial insert, with a bearing surface, adapted to be positioned on the top side of the tibial plateau, a femoral component having a base portion and a central housing, the femoral component having an axis of extension-flexion rotation, the base portion having a pair of condyles, an a mechanical linkage component linking the tibial component with the femoral component and with the tibial insert in between the tibial component and the femoral
(Continued)

component, so that there is a center of contact between the condyles and the bearing surface.

21 Claims, 7 Drawing Sheets

Related U.S. Application Data continuation of application No. 13/963,306, filed on Aug. 9, 2013, now Pat. No. 9,056,012, which is a continuation of application No. 12/353,295, filed on Jan. 14, 2009, now Pat. No. 8,545,570, which is a continuation of application No. 10/499,047, filed as application No. PCT/US02/41221 on Dec. 20, 2002, now Pat. No. 7,572,292.

(60) Provisional application No. 60/342,350, filed on Dec. 21, 2001.

(51) Int. Cl.
    *A61F 2/46*     (2006.01)
    *A61F 2/30*     (2006.01)

(52) U.S. Cl.
CPC ............ *A61F 2/389* (2013.01); *A61F 2/3854* (2013.01); *A61F 2/3859* (2013.01); *A61B 17/1659* (2013.01); *A61F 2/3868* (2013.01); *A61F 2/4684* (2013.01); *A61F 2002/30034* (2013.01); *A61F 2002/30062* (2013.01); *A61F 2002/30131* (2013.01); *A61F 2002/30332* (2013.01); *A61F 2002/30433* (2013.01); *A61F 2002/30497* (2013.01); *A61F 2002/30563* (2013.01); *A61F 2002/30604* (2013.01); *A61F 2002/30878* (2013.01); *A61F 2002/30884* (2013.01); *A61F 2210/0004* (2013.01); *A61F 2220/0025* (2013.01); *A61F 2220/0033* (2013.01); *A61F 2220/0041* (2013.01); *A61F 2230/0013* (2013.01)

(56) References Cited

U.S. PATENT DOCUMENTS

| | | | |
|---|---|---|---|
| 3,837,009 A | | 9/1974 | Walker |
| 3,934,272 A | | 1/1976 | Wearne et al. |
| 4,136,405 A | * | 1/1979 | Pastrick ............ A61F 2/384 623/20.25 |
| 4,213,209 A | | 7/1980 | Insall et al. |
| 4,219,893 A | * | 9/1980 | Noiles ............ A61F 2/3836 623/20.25 |
| 4,262,368 A | | 4/1981 | Lacey |
| 4,301,553 A | | 11/1981 | Noiles |
| 4,358,859 A | | 11/1982 | Schurman et al. |
| 4,462,120 A | | 7/1984 | Rambert et al. |
| 4,538,305 A | | 9/1985 | Englebrecht et al. |
| 4,662,889 A | | 5/1987 | Zichner et al. |
| 4,770,663 A | | 9/1988 | Hanslik et al. |
| 4,834,758 A | | 5/1989 | Lane et al. |
| 4,865,606 A | | 9/1989 | Rehder |
| 5,147,405 A | | 9/1992 | Van Zile et al. |
| 5,147,406 A | | 9/1992 | Houston et al. |
| 5,181,925 A | | 1/1993 | Houston et al. |
| 5,236,461 A | | 8/1993 | Forte |
| 5,314,481 A | | 5/1994 | Bianco |
| 5,358,527 A | | 10/1994 | Forte |
| 5,370,701 A | * | 12/1994 | Finn ............ A61F 2/385 623/20.25 |
| 5,405,398 A | | 4/1995 | Buford et al. |
| 5,411,555 A | | 5/1995 | Nieder |
| 5,413,607 A | | 5/1995 | Englebrecht et al. |
| 5,549,689 A | | 8/1996 | Epstein et al. |
| 5,702,466 A | | 12/1997 | Pappas et al. |
| 5,755,804 A | | 5/1998 | Schmotzer et al. |
| 5,766,257 A | | 6/1998 | Goodman et al. |
| 5,782,921 A | | 7/1998 | Colleran et al. |
| 5,782,925 A | | 7/1998 | Collazo et al. |
| 5,800,552 A | | 9/1998 | Forte |
| 5,824,096 A | | 10/1998 | Pappas et al. |
| 5,824,102 A | | 10/1998 | Buscayret |
| 5,954,770 A | | 9/1999 | Schmotzer et al. |
| 6,019,794 A | | 2/2000 | Walker |
| 6,068,658 A | | 5/2000 | Insall et al. |
| 6,099,570 A | | 8/2000 | Livet et al. |
| 6,143,034 A | | 11/2000 | Burrows |
| 6,165,223 A | | 12/2000 | Metzger et al. |
| 6,264,696 B1 | | 7/2001 | Reigner et al. |
| 6,485,519 B2 | | 11/2002 | Meyers et al. |
| 6,770,097 B2 | | 8/2004 | Leclerq |
| 6,773,461 B2 | | 8/2004 | Meyers et al. |
| 6,984,249 B2 | | 1/2006 | Keller |
| 6,986,791 B1 | | 1/2006 | Metzger |
| 7,160,330 B2 | | 1/2007 | Axelson et al. |
| 7,297,165 B1 | | 11/2007 | Kriek |
| 7,572,292 B2 | | 8/2009 | Crabtree et al. |
| 7,658,767 B2 | | 2/2010 | Wyss |
| 7,871,442 B2 | | 1/2011 | Servidio |
| 2001/0001121 A1 | | 5/2001 | Lombardo et al. |
| 2002/0103541 A1 | | 8/2002 | Meyers et al. |
| 2002/0107576 A1 | | 8/2002 | Meyers et al. |
| 2003/0009228 A1 | | 1/2003 | Meyers |
| 2004/0143339 A1 | | 7/2004 | Axelson et al. |
| 2004/0186584 A1 | | 9/2004 | Keller |
| 2004/0249467 A1 | | 12/2004 | Meyers et al. |
| 2005/0107886 A1 | | 5/2005 | Crabtree et al. |
| 2005/0246028 A1 | | 11/2005 | Pappas et al. |
| 2008/0119940 A1 | | 5/2008 | Otto et al. |
| 2008/0167722 A1 | | 7/2008 | Metzger et al. |
| 2009/0088860 A1 | | 4/2009 | Romeis et al. |
| 2009/0125114 A1 | | 5/2009 | May et al. |
| 2009/0143866 A1 | | 6/2009 | Servidio |
| 2010/0016977 A1 | | 1/2010 | Masini |

FOREIGN PATENT DOCUMENTS

| | | |
|---|---|---|
| DE | 19915053 | 10/1999 |
| DE | 10012059 | 10/2002 |
| DE | 102005015598 | 9/2006 |
| EP | 69683 | 1/1983 |
| EP | 194326 | 9/1986 |
| EP | 336774 | 10/1989 |
| EP | 420460 | 4/1991 |
| EP | 472475 | 2/1992 |
| EP | 653194 | 5/1995 |
| EP | 510299 | 8/1995 |
| EP | 553585 | 11/1995 |
| EP | 716839 | 6/1996 |
| EP | 925766 | 6/1996 |
| EP | 724868 | 8/1996 |
| EP | 988840 | 3/2000 |
| EP | 1038286 | 9/2000 |
| EP | 916321 | 6/2003 |
| EP | 970667 | 12/2003 |
| EP | 1285638 | 12/2003 |
| EP | 1447060 | 8/2004 |
| EP | 1721584 | 11/2006 |
| EP | 1721585 | 12/2006 |
| EP | 2213262 | 8/2010 |
| FR | 2508793 | 10/1983 |
| FR | 2710835 | 4/1995 |
| FR | 2776919 | 9/2000 |
| GB | 1363018 | 8/1974 |
| GB | 1409150 | 10/1975 |
| GB | 2324249 | 12/2001 |
| GB | 2335145 | 12/2002 |
| JP | 8500992 | 2/1996 |
| JP | 8224263 | 9/1996 |
| JP | 10501155 | 2/1998 |
| JP | 04951797 | 6/2012 |
| WO | WO9532623 | 12/1995 |

(56) References Cited

FOREIGN PATENT DOCUMENTS

| WO | WO0113825 | 3/2001 |
|----|-----------|--------|
| WO | WO03059203 | 7/2003 |
| WO | WO2009056836 | 5/2009 |

OTHER PUBLICATIONS

Brochure entitled Aesculap EnduRo Gekoppelte Knieendoprothese Operationalstechnik Aesculap Orthopaedics B/Braun Sharing Expertise, 56 pages, known prior to Jul. 16, 2010.
Brochure entitled Aesculap EnduRo Rotating Hinge Knee Endoprothesis Manual Surgical Procedure B/Braun Sharing Expertise, 1 page, known prior to Jul. 16, 2010.
Photopgrah of Aesculap-B Braun EnduRo Knee—rotating hinge (known prior to Jul. 16, 2010).
Office Action dated May 4, 2007 in related U.S. Appl. No. 10/499,047.
Response dated Nov. 5, 2007 in related U.S. Appl. No. 10/499,047.
Office Action dated Jan. 24, 2008 in related U.S. Appl. No. 10/499,047.
Response dated Apr. 24, 2008 in related U.S. Appl. No. 10/499,047.
Office Action dated May 13, 2008 in related U.S. Appl. No. 10/499,047.
Response dated Aug. 13, 2008 in related U.S. Appl. No. 10/499,047.
Notice of Allowance dated Oct. 8, 2008 in related U.S. Appl. No. 10/499,047.
International Search Report for International Application No. PCT/US2007/072611, mailed Nov. 23, 2007, 4 pages.
First Office Action for Chinese Application No. 20780025036.3, mailed Dec. 7, 2010, 8 pages.
Communication Pursuant to Article 94(3) EPC for European Application No. 07799226.1, mailed Jul. 8, 2010, 4 pages.
International Search Report for International Application No. PCT/US202/41221, mailed Oct. 10, 2003, 3 pages.
English-Language Translation of EP472475, translated May 23, 2012, with certification of translation, 11 pages.
Notice of Reasons for Rejection for Japanese Application No. 2009-518598, mailed Jun. 26, 2012.
Office Action for U.S. Appl. No. 12/307,102, mailed Aug. 9, 2012.
Office Action for Canadian Application No. 2,656,359, mailed Jul. 8, 2014.
Notice of Reasons for Rejection for Japanese Application No. 2013-096941, mailed Apr. 7, 2014.
Patent Examination Report No. 2 for Australian Application No. 2007269203, mailed Feb. 12, 2014.
Communication Pursuant to Article 96(2) EPC for European Application No. 02798579.5, mailed Mar. 15, 2005.
International Preliminary Report on Patentability for Internaitonal Application No. PCT/US2007/072611, mailed Jan. 6, 2009.
Gschwend, N., "GSB Knee Joint," Clinical Orthopaedics and Related Research, No. 132, May 1978, pp. 170-176.
Communication Pursuant to Article 94(3) EPC for European Application No. 07799226.1, mailed Aug. 29, 2014.
Office Action for Canadian Application No. 2,656,359, mailed Nov. 13, 2015.

* cited by examiner

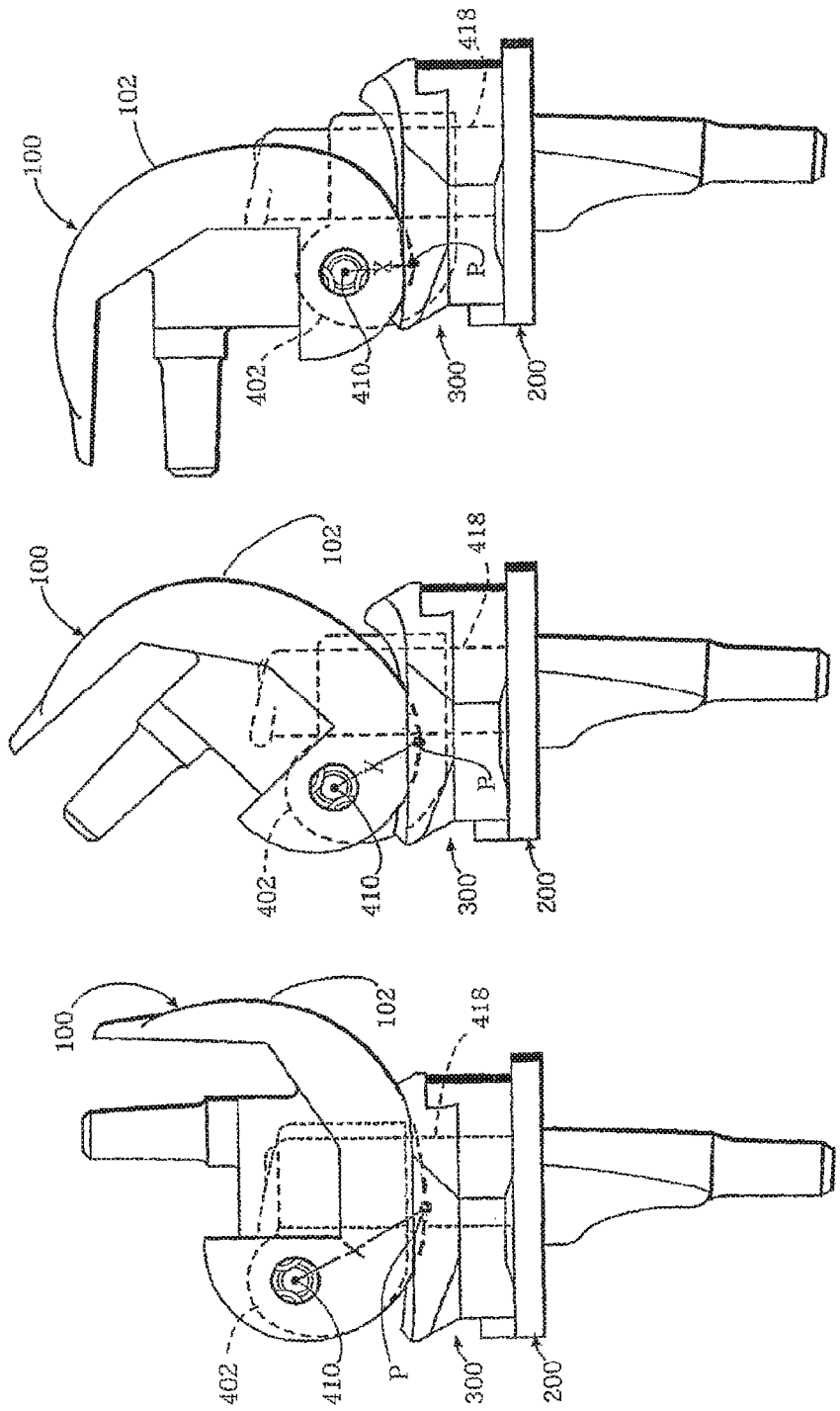

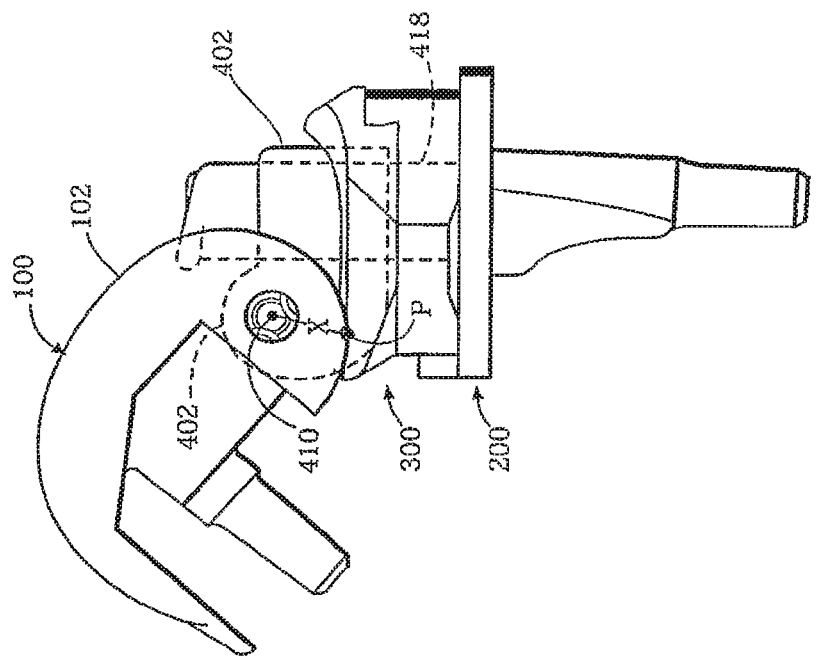
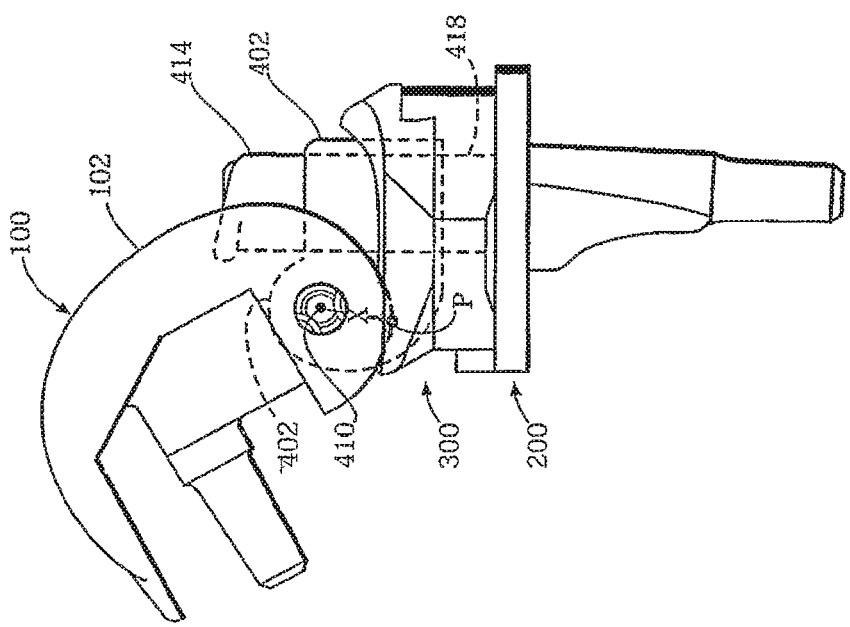

HINGED JOINT SYSTEM

CROSS-REFERENCE TO RELATED APPLICATIONS

This application is a is a continuation of U.S. patent application Ser. No. 14/714,568, filed May 18, 2015, now allowed, which is a continuation of U.S. patent application Ser. No. 13/963,306, filed Aug. 9, 2013, now U.S. Pat. No. 9,056,012, issued Jun. 16, 2015, which is a continuation of U.S. patent application Ser. No. 12/353,295, filed Jan. 14, 2009, now U.S. Pat. No. 8,545,570, issued Oct. 1, 2013, which is a continuation of U.S. patent application Ser. No. 10/499,047, filed Jun. 16, 2004, now U.S. Pat. No. 7,572,292, issued Aug. 11, 2009, which is a national phase of International Application No. PCT/US02/41221, filed Dec. 20, 2002, which claims priority from U.S. Provisional Application No. 60/342,350 filed Dec. 21, 2001. The contents of the prior applications are incorporated herein by reference in their entirety.

FIELD OF THE INVENTION

The present invention relates to prosthetic joints, and more particularly to a hinged joint that allows for the natural kinematics of the joint.

BACKGROUND OF THE INVENTION

In primary knee joint replacement surgery, a surgeon typically affixes two prosthetic components to the patient's bone structure; a first to the patient's femur and a second to the patient's tibia. These components are typically known as the femoral component and the tibial component respectively. In a typical primary knee joint replacement surgery the ligaments and tendons are sufficiently intact to control the movement of the knee.

The femoral component is placed on a patient's distal femur after appropriate resection of the femur. The femoral component is usually metallic, having a highly polished outer condylar articulating surface, which is commonly J-shaped.

A common type of tibial component uses a tray or plateau that generally conforms to the patient's resected proximal tibia. The tibial component also usually includes a stem which extends at an angle to the plateau in order to extend into a surgically formed opening in the patient's intramedullary canal. The tibial component and tibial stem are both usually metallic.

A plastic or polymeric (often ultra high molecular weight polyethylene or UHMWPE) insert or bearing fits between the tray of the tibial component and the femoral component. This tibial insert provides a surface against which the femoral component condylar portion articulates—moves in gross motion corresponding generally to the motion of the femur relative to the tibia.

In some knee prostheses, the tibial insert also engages in motion relative to the tibial tray. Such motion can be translational and-or rotational sliding motion relative to the tibial plateau. In other types of knee prostheses with tibial inserts, the tibial inserts can engage in other types of motion relative to the tibial plateau and-or femoral component.

Revision surgery is required when the primary prosthesis fails. In most revision cases additional stabilization and structure are necessary to compensate for loss of bone and soft tissue. For example, the femoral and tibial components may be thicker to make up for the loss of bone. The femoral component may include a stem, which generally extends at about six degrees from perpendicular from the base portion of the femoral component in order to extend into a surgically formed opening in the patient's intramedullary canal. In order to provide increased stabilization, a box may be provided on the femoral component and a mating post on the tibial component, creating what is called a constrained knee replacement.

In some cases, the loss of soft tissue in the knee requires the use of a linked or hinged knee prosthesis. The three most common indications that a hinged knee is necessary are: (1) in an increasing number of revision cases, the patient loses too much bone and soft tissue to use a constrained knee; (2) an oncologist may be forced to resect a large portion of a bone in order to remove a tumor; and (3) in trauma applications, often the distal femur or proximal tibia has been crushed and must be replaced.

Early hinged knees were fixed, allowing no internal-external rotation. These early hinges had a history of loosening because their fixation could not adequately handle applied forces. Rotating hinges decreased this failure because these rotating hinges minimized internal-external rotational torque. Hinged knee systems provide a physical link of two components with an axle, such that all medial-lateral and anterior-posterior stability is provided by the prosthesis. These systems also address various degrees of bone loss. During normal articulation, the pivot axis for the axle is fixed in the anterior-posterior and superior-inferior directions, so that when the knee is flexed or extended about the axle the center of contact between the femoral and tibial components is fixed. This prevents roll-back.

A major concern with hinged knees is simulating the movement of a natural knee joint. The movement of a natural knee joint has three translations: anterior-posterior, medial-lateral, and inferior-superior and three rotations: flexion-extension, internal-external, and abduction-adduction. The movements of the knee joint are determined by the shape of the articulating surfaces of the tibia and femur and the orientation of the major ligaments of the knee joint, including the anterior and posterior cruciate ligaments and the medial and lateral collateral ligaments as a four linkage system. Knee flexion-extension involves a combination of rolling and sliding of the femur on the tibial plateau called femoral roll-back. In roll-back during flexion, the center of contact between the femur and the tibial plateau moves posteriorly, which allows increased ranges of flexion and increased efficiency of the extensor mechanism.

Current hinged knees typically allow both hinge-over in the flexion-extension direction and internal-external rotation, but do so by flexing about a fixed pivot axis that eliminates roll-back. Some hinged knee designs, on the other hand, have hinge mechanisms that allow roll-back, but do not control roll-back. No known hinged knee systems both allow and control roll-back.

During pre-op planning the extent of bone and soft tissue damage is not always discernible. Since surgical preference typically is to use the least intrusive procedure, a revision with a constrained prosthesis, as opposed to a hinge knee, is preferred. If, during surgery, it becomes apparent that a hinge knee is necessary, it would be preferable for the hinge to be part of an integrated system so the surgeon can proceed with minimal interruptions. Current hinged systems are stand alone, so that if the surgeon plans to use a constrained knee but realizes during surgery that the added constraint of a hinged knee is required, the surgeon cannot switch to a hinged knee during the procedure. Rather, the surgeon typically has to start another procedure resulting in longer operating times and greater risk to the patient. Additionally, current hinged knees require the surgeon to remove a large portion of the patient's bone in order to allow proper implantation.

Current hinged knee systems require a considerable amount of assembly during surgery in order to ensure that the various components are properly sized and connected. Such assembly takes time, is tedious and prone to error, and averts the surgeon's attention from more critical matters directly related to the health of the patient.

Thus, there is a current need for a hinged knee prosthesis that provides natural kinematics without excessive bone removal. There is also a need for a hinged knee system that is compatible with existing total knee replacement systems. Finally, there is a need for a hinged knee system that requires less assembly during surgery.

SUMMARY OF THE INVENTION

Methods, systems, and devices for replacement of a joint with a prosthetic system that replicates the natural kinematics of the joint are disclosed. Methods, systems, and devices according to the invention not only allow, but also control, the roll-back and kinematics of the prosthesis, and thus the joint, and provide both natural biomechanics and joint performance. Some existing hinged knee designs provide linked articulation in substitution for soft tissue deficiencies, but do so by flexing about a fixed pivot axis eliminating roll-back. The prior art that allows movement of the axis of rotation or axle allows the axle to move in the anterior and posterior directions, but does not control the movement. Some prior art discloses an axis of rotation near the center of the femoral component and other prior art discloses an axis of rotation in the rear portion of the femoral component. This prior art allows the femoral component and femur to move in the anterior and posterior directions relative to the tibia, but does not control the movement. The present invention controls roll-back through the operation of its linkage component. A prosthetic system according to one embodiment of the invention includes a tibial component having a tibial plateau and a tibial stem portion, the tibial plateau having a top side and a bottom side, a tibial insert, with a bearing surface, adapted to be positioned on the top side of the tibial plateau, a femoral component having a base portion, a central housing and a femoral stem portion, the femoral component having an axis of extension-flexion rotation, the base portion having a pair of condyles, a mechanical linkage component linking the tibial component with the femoral component and with the tibial insert in between the tibial component and the femoral component, so that there is a center of contact between the condyles and the bearing surface, the mechanical linkage component adapted to allow the center of contact to move posteriorly during flexion, provide for the movement of the axis of extension-flexion rotation in the superior-inferior direction, allow rotation of the tibial component, the tibial insert, and the femoral component about a superior-inferior axis, and offset the axis of extension-flexion rotation from the superior-inferior axis in order to provide and control the natural kinematics of the knee joint.

A prosthetic system according to one embodiment of the invention includes a mechanical linkage component linking the tibial component with the femoral component and with the tibial insert in between the tibial component and the femoral component so that there is a center of contact between the condyles and the bearing surface, the mechanical linkage component adapted to move in the superior-inferior directions and restrained from movement in the anterior-posterior directions, wherein the center of contact between the condyles and bearing surface moves in the anterior-posterior direction as the femoral component moves through extension and flexion.

A prosthetic system according to one embodiment of the invention includes a tibial component having a tibial plateau and a tibial stem portion, the tibial plateau having a top side and a bottom side, a post having a proximal end and a distal end, the post adapted to project from the top side of the tibial plateau, a cap adapted to mount on the proximal end of the post, a tibial insert having an aperture, the tibial insert adapted to be positioned on the top side of the tibial plateau with the tibial insert aperture adapted to receive the post and the cap, a femoral component having a base portion and a central housing having a femoral stem portion, the base portion having a pair of condyles and two posteriorly extending lobes, an axle adapted to connect to the lobes and extend between the lobes, and a link having an anterior end and a posterior end, the link adapted to be connected to the axle at the posterior link end and to receive the post and the cap at the anterior link end.

A method for replacing a joint with a prosthetic system according to one embodiment of the invention includes resecting the proximal end of the patient's tibia to expose the tibial intramedullary canal of the tibia, resecting the distal end of the patient's femur to expose the femoral intramedullary canal, connecting a tibial stem and a femoral stem to a prosthetic system, the prosthetic system having a mechanical linkage component, inserting the tibial stem into the tibial intramedullary canal, and inserting the femoral stem into the femoral intramedullary canal. The method allows a surgeon to convert to the prosthetic system from a primary or revision prosthesis with common bone cuts and instrumentation. The prosthetic system allows the surgeon to select an appropriately sized tibial insert and a cap so that a pre-assembled femoral component can be used, thereby significantly reducing the amount of surgical time devoted to assembly of the knee.

Another feature of the present invention is that a bioresorbable bumper can be placed in the prosthetic system to prevent rotation of the prosthetic components around a superior-inferior axis until the bumper is resorbed by the body.

BRIEF DESCRIPTION OF THE DRAWINGS

FIGS. 6A-E are side views of an embodiment of the prosthesis progressing from extension in FIG. 6A to flexion in FIG. 6E.

DETAILED DESCRIPTION

Figure 1A:
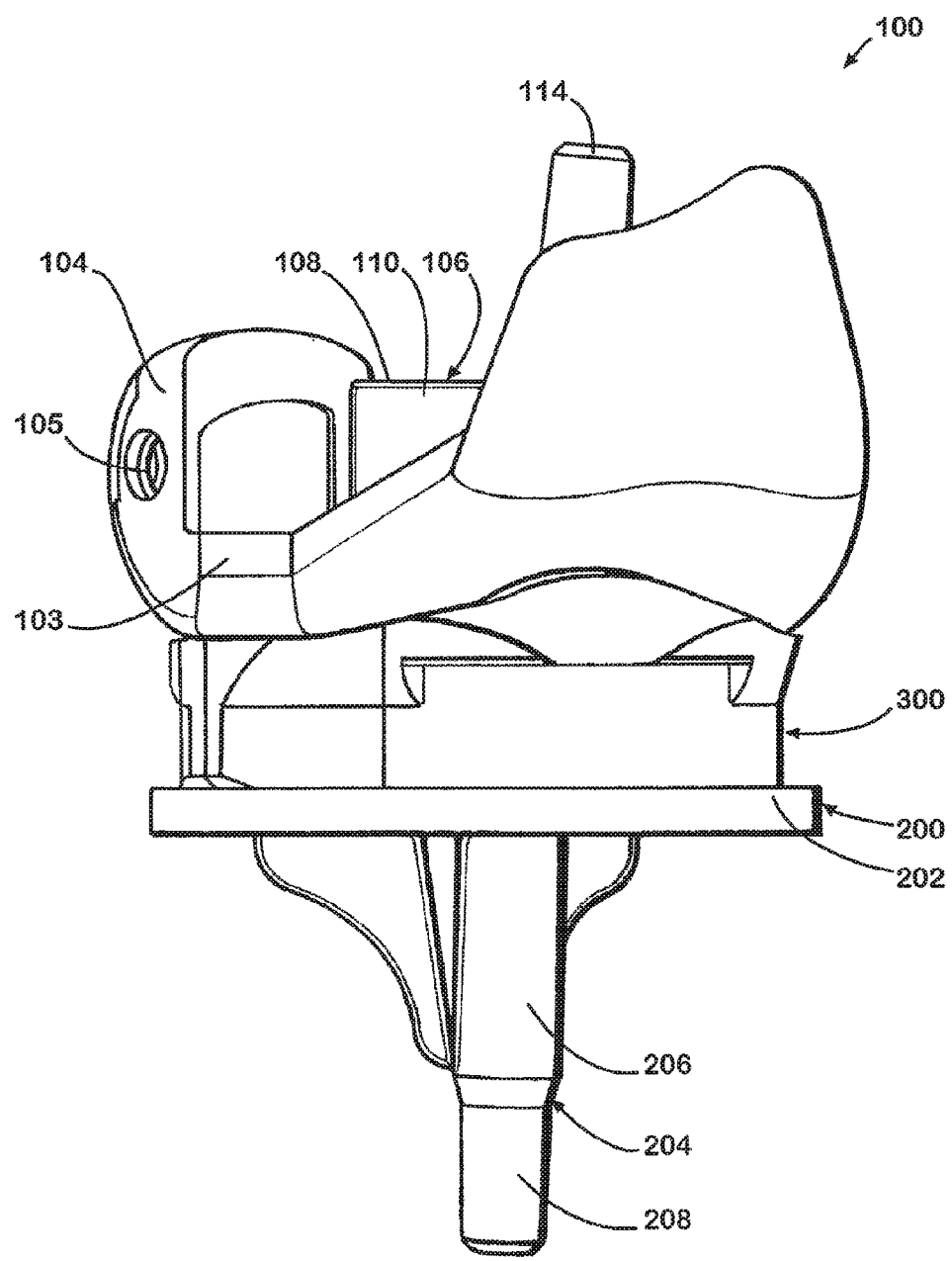
FIG. 1A is an anterior perspective view of an embodiment of the invention showing the prosthetic system in extension.
Figure 1B:
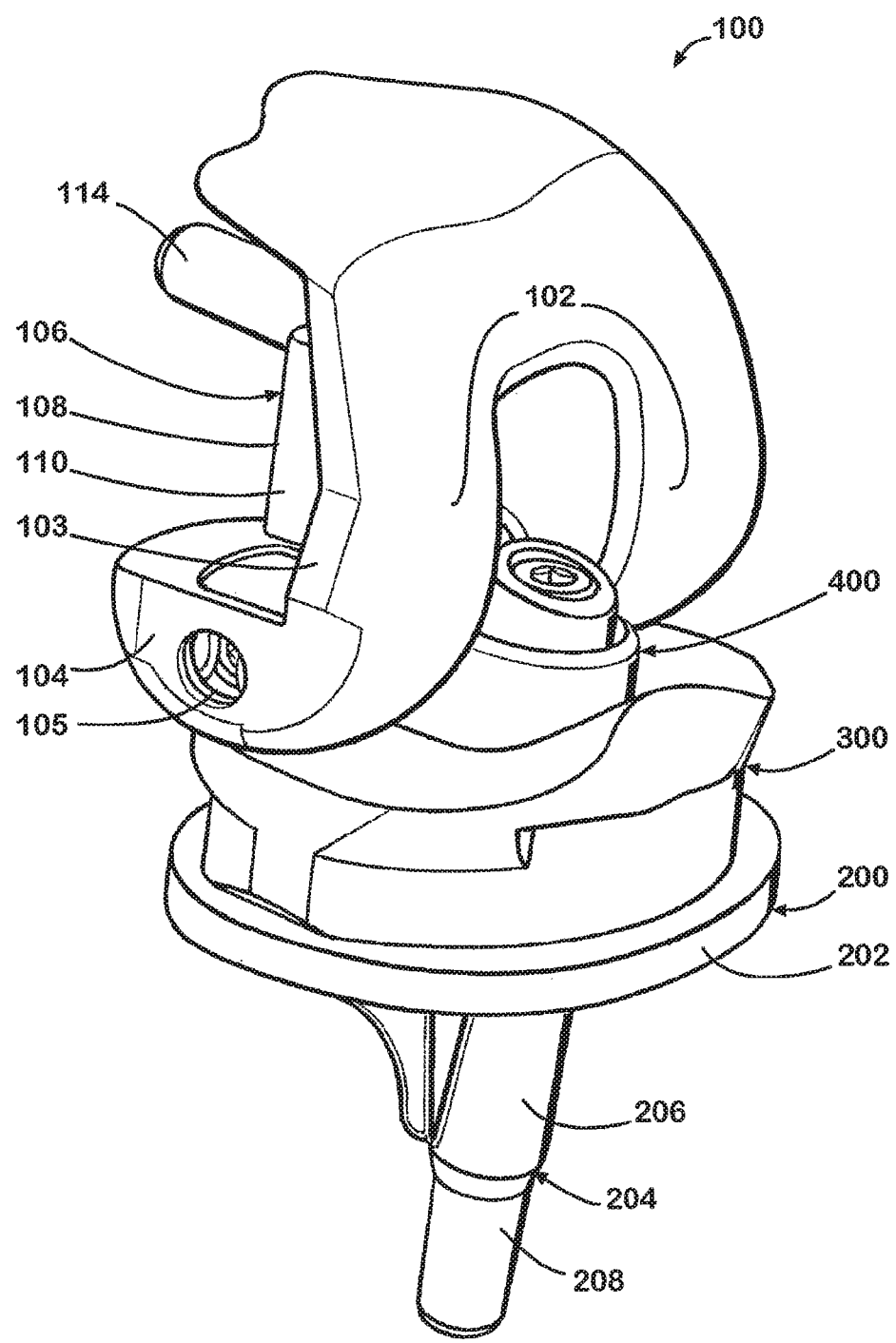
FIG. 1B is an anterior perspective view of the embodiment shown in FIG. 1A, showing the prosthetic system in flexion.
Figure 2:
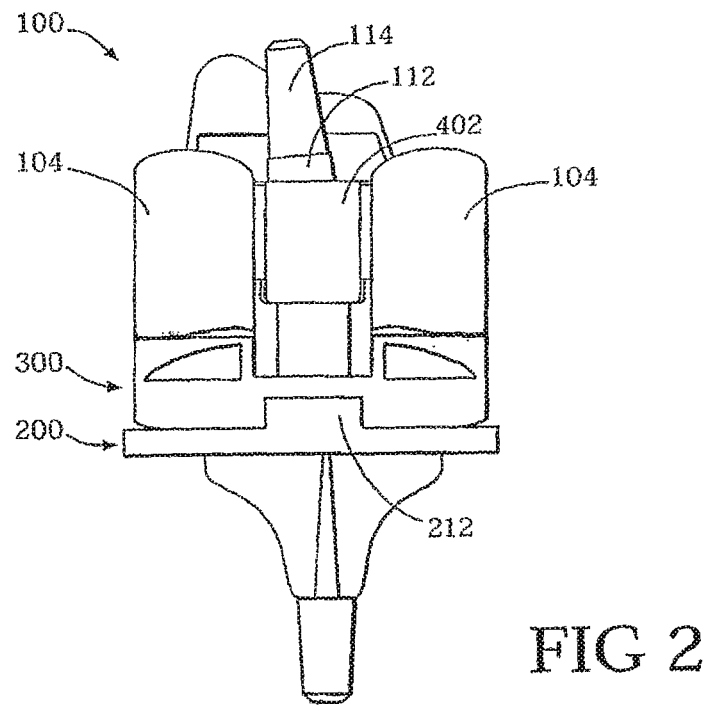
FIG. 2 is a posterior view of an embodiment of the prosthesis.
Figure 3:
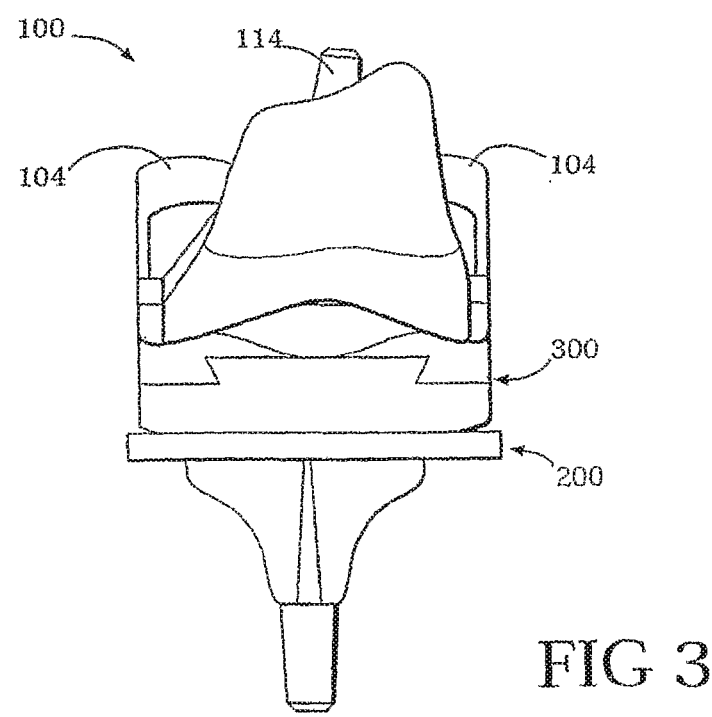
FIG. 3 is an anterior view of an embodiment of the prosthesis.
Figure 4:
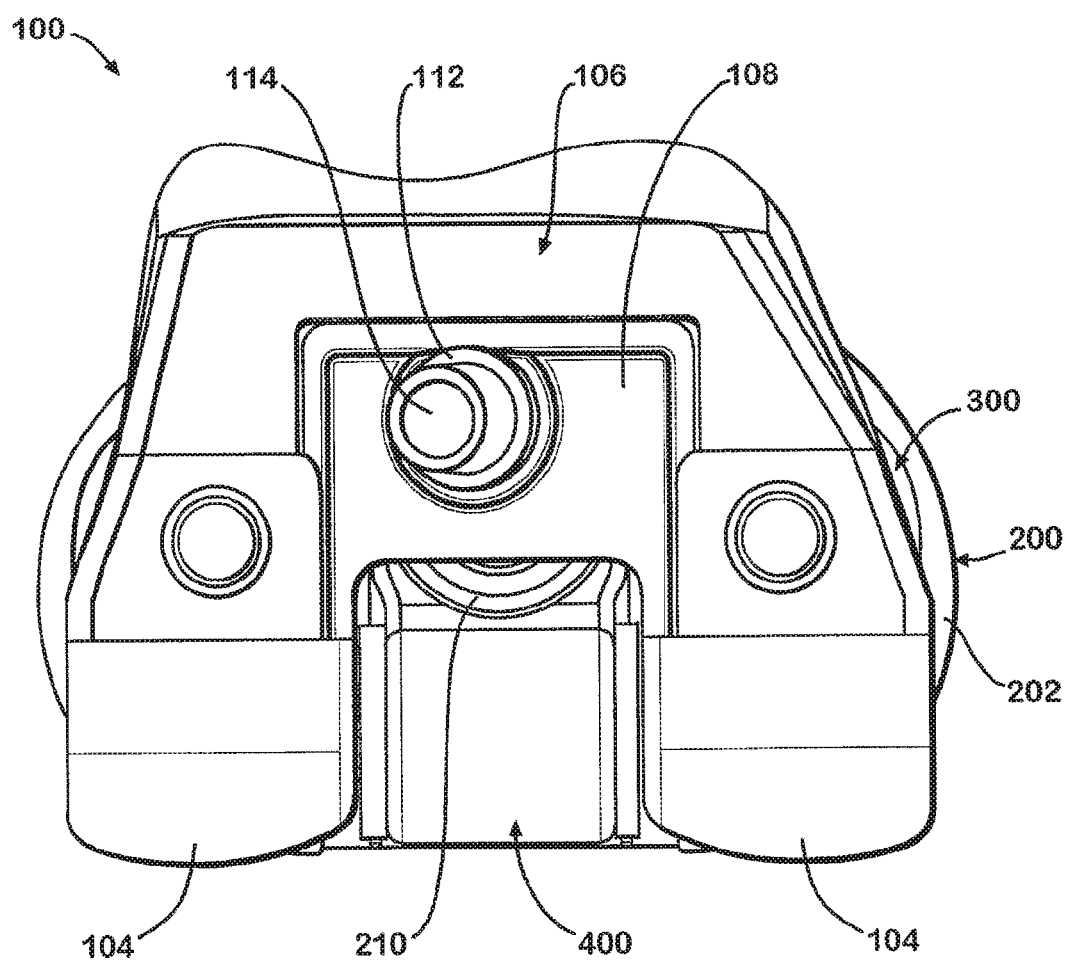
FIG. 4 is a top view of an embodiment of the prosthesis.

FIG. 1 illustrates a perspective view of an embodiment of a prosthetic system in extension in FIG. 1A and at 90° flexion in FIG. 1B. FIGS. 2 and 3 show a posterior view and an anterior view, respectively, of an embodiment of the prosthetic system in extension. FIG. 4 shows a top view of an embodiment of the prosthetic system in extension. While the illustrated embodiment is a knee joint, the present invention could be used in other joints, such as a hip joint or a shoulder joint. The prosthetic system includes a femoral component 100, a tibial component 200, a tibial insert 300, and a mechanical linkage component or hinge portion 400. In surgery with the prosthetic system, the tibia and femur are recessed with the intramedullary canals of the tibia and the femur surgically prepared to receive stems. The present invention requires the same bone cuts and instrumentation as a primary or revision system, such as, for example, the Genesis II total knee system from Smith & Nephew. Only one additional cut is necessary with the present invention.

The tibial component 200 includes a tibial plateau 202 and a tibial stem portion 204. The tibial stem portion 204 includes a generally cylindrical portion 206 integrally formed with distal end 208 which comprises a Morse taper. The distal end 208 can have a long stem attached (not shown) via the Morse taper in a manner well known to those skilled in the art. Distal end 208 is fitted into the intramedullary canal of the resected tibia, either with or without a long stem attached to the Morse taper.

The femoral component 100 includes a pair of condyles 102, which are metallic and highly polished and formed on a base portion 103 of the femoral component 100. The condyles 102 engage with the tibial insert 300. The femoral component 100 has a J-shaped cross section and as a result has J-shaped condylar surfaces 102. These J-shaped surfaces have at least two different radii of curvature: a distal radius and a posterior radius. In the preferred embodiment shown, the distal radius of curvature is larger than the posterior radius of curvature. The base portion 103 includes a pair of posteriorly extending lobes 104 that connect to the hinge element 400 as described below. Integral with and positioned between the condylar portions is a central housing 106 having a top wall 108 and side walls 110. Angularly mounted from the top wall 108 is a femoral stem portion 112 having a proximal end 114 comprising a Morse taper. The proximal end 114 can have a long stem attached (not shown) via the Morse taper in a manner well known to those skilled in the art, or can be used without a long stem. The proximal end 114 of the stem portion 112 is inserted into the intramedullary canal of the resected femur, either with or without a long stem attached to the Morse taper.

For simplicity, the preferred embodiment is described as having two radii of curvature along the distal and posterior surfaces of femoral component 100, with the distal radius being larger than the posterior radius, as discussed above. It is to be understood that it may be advantageous to incorporate one or more additional radii of curvature along the outer surface of the femoral component. In particular, a third radius may be used to form the curvature at the proximal surface of lobes 104 of the posterior condyles. The number and relationship of the radii of curvature may be varied without departing from the spirit and scope of this invention.

Figure 5:
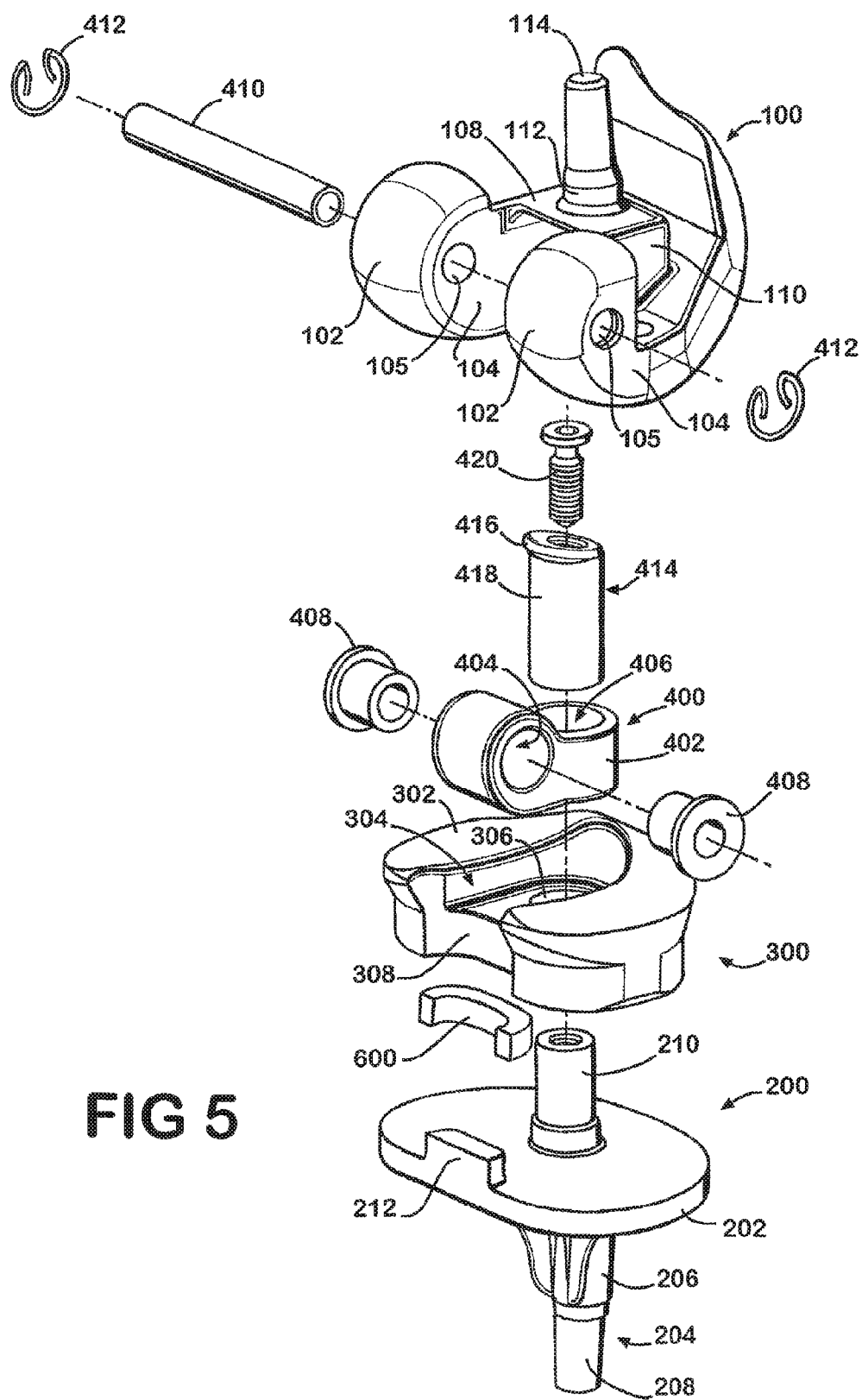
FIG. 5 is a posterior exploded view of an embodiment of the invention.

FIG. 5 is an exploded posterior perspective view of an embodiment of the prosthetic system. A post 210 is positioned on the top side of the tibial plateau 202 in the vertical (superior-inferior) direction perpendicular to the tibial plateau 202 and a stop 212 is positioned at the posterior portion of the tibial plateau 202. The post 210 receives a cap 414. The cap 414 is secured to the post 210 via a fastener 420 or any other method known to those skilled in the art.

The tibial insert 300 has a top bearing surface 302 and a recessed portion 304 with an aperture 306 and a notch 308. The tibial insert aperture 306 receives the tibial post 210 and cap 414 so that the tibial insert 300 is situated on the tibial plateau 202. In the illustrated embodiment, the tibial insert rotates about the vertical (superior-inferior) axis. The rotation of the tibial insert is controlled by the notch 308 at the posterior of the tibial insert 300 and the stop 212 of the tibial plateau 202. The condyles of the femoral component translate on the bearing surface 302 of the tibial insert 300.

The hinge portion 400 includes a link 402 with an aperture 404 in the medial-lateral direction on the posterior end and an aperture 406 in the superior-inferior direction on the anterior end. Two bushings 408 fit into the ends of the posterior aperture 404. The posterior end of the link 402 is positioned between the lobes 104 of the femoral component 100. The link 402 is rotatably connected to the femoral component by an axle 410 positioned in apertures 105 of both lobes 104 of the femoral component 100 and through the posterior aperture 404 and bushings 408 of the link. The axle 410 is secured to the lobes 104 via two axle clips 412 on each end of the axle 410. Alternatively, the axle 410 could be secured to the lobes 104 via any method known to those skilled in the art. The anterior aperture 406 of the link receives the tibial post 210 and cap 414. The link 402 translates up and down the post 210 and cap 414 and rotates about the superior-inferior axis. The cap 414 has a sheath portion 418 and a lip portion 416 that is positioned at its proximal end. Alternatively, the cap 414 could fit only on the top of the tibial post 210 and not have a sheath portion. The anterior aperture 406 of the link 402 has a smaller diameter in its distal half so that the lip 416 of the cap 414 catches on the smaller diameter and controls the translation of the link 402.

The cap 414 is a separate piece and different sizes are available to correspond with the thickness of the tibial insert 300. This allows the femoral component to be pre-assembled and allows the surgeon to select the appropriate cap size and tibial insert size during surgery to allow for proper operation of the prosthetic system. This differs from most systems where the surgeon must assemble the femoral component based on the tibial insert size.

As demonstrated by FIG. 6, the operation of the hinge portion 400 allows femoral roll-back and controls this movement. FIG. 6 shows the prosthetic system moving from full extension (0° flexion) in FIG. 6A to 140° flexion in FIG. 6E. The prosthetic system is in 45° flexion in FIG. 6B, 90° flexion in FIG. 6C, and 120° flexion in FIG. 6D. As shown in FIG. 6A, when the knee is in extension the link 402 is towards the top of the tibial post 210 and cap 414. Distraction is prevented by the cap 414 of the tibial post 210 catching on the inner diameter of the anterior link aperture 406. As the knee moves from extension to flexion the link 402 moves down the tibial post 210 and cap 414. The link 402 does not move in the anterior-posterior directions, which allows the axle 410 to move only along the superior-inferior axis.

As shown in FIG. 6, the axle moves in the inferior direction when the knee moves from extension to flexion and moves in the superior direction when the knee moves from flexion to extension. Axle 410 moves inferiorly until posterior movement of the femoral component 100 positions femoral component 100 so that it rides up the posterior lip of tibial insert 300, then axle 410 moves superiorly. In the embodiment shown, this translates into inferior movement of axle 410 when the knee move from 0° to about 90° flexion, no vertical movement of axle 410 from about 90° to about 120°, and superior movement from about 120° to about 140° flexion. The exact motion of axle 410 through the range of knee flexion may change depending on the size of the components and other design features not critical to this invention.

The center of contact of the condyles 102 on the bearing surface 302 moves in the posterior direction as the knee moves from extension to flexion and moves in the anterior direction when the knee moves from flexion to extension. In FIG. 6, P represents the center of contact of the condyles and the bearing surface. Because the radius of curvature of the condyles decreases when the knee moves from extension to flexion, the distance X from the center of contact P to the center point of the axle decreases from extension to flexion, up to about 120° of flexion in the embodiment shown.

The freedom of the axle 410 to move superiorly-inferiorly while linking the femoral and tibial components via the link 402 and the offset of axle 410 relative to the center of rotation of the femoral component 100 result in roll-back of the femoral component during flexion while maintaining contact between the femoral component and the tibial insert 300. Increasing the posterior offset of the axle 410 from the center of rotation of the femoral component 100 causes an increasing anterior shift in the center of contact P between the femoral component 100 and the tibial insert 300 in extension and increasing travel of the link 402 down the post 210 and cap 414 in flexion. Increasing inferior offset of the axle 410 from the center of rotation of the femoral component 100 causes an increasing posterior shift in the center of contact between the femoral component and the tibial insert in flexion and decreasing travel of the link 402 up the post 210 and cap 414 in extension.

The ability of the link 402 to travel superiorly-inferiorly on the tibial post 210 and cap 414 allows specific combinations of link length, anterior-posterior offset and superior-inferior offset of the axle 410 so that the anterior-posterior location of the center of contact between the femoral component and the tibial insert as a function of flexion can be specified and controlled. For example, less roll-back may be desirable for smaller sized knees. This motion is further tailored by combining the above described movement with the two different radii of curvature (larger distally and smaller posteriorly) in the condyle section of the femoral component—illustrated by decrease of the distance X as the knee moves from extension to flexion in FIG. 6. Depending on the specific objectives regarding the occurrence of roll-back during flexion, a hinge knee could be designed according to this invention having a single radius of curvature on the femoral component, or two or more radii of curvature. While two radii are shown in the preferred embodiment, it is to be understood that the principles of this invention are not to be so limited.

In specifying the motion as a function of flexion (kinematics), the performance of muscle and other soft tissues can be optimized. For example, femoral roll-back is recognized as improving efficiency of the extensor mechanism. In general, roll-back is a posterior shift in the center of contact of the femoral component on the tibial component as the knee flexes and an anterior shift in the center of contact of the femoral component on the tibial component as the knee extends. Three parameters define and control kinematics, including roll-back, in the prosthetic system of the current invention. The first parameter is the anterior-posterior and superior-inferior placement of the axle in the femoral condyles. With the first parameter, the axis of rotation is positioned in the posterior portion of the femoral component, without imposing undue structural load away from the natural load axis of the knee bone structure. This way the load axis is not skewed in the anterior-posterior or medial-lateral direction from natural load axis of tibia. The second parameter is the two different radii of curvature in the J-curve section of the femoral component. The third parameter is the length of the link. Tailoring these parameters according to the implant type and size optimizes the kinematics and joint performance and allows control of roll-back.

The prosthetic system additionally does not allow subluxation in the medial-lateral directions or in the anterior-posterior directions, because the tibial component is mechanically linked to the femoral component.

The prosthetic system according to one embodiment shares common design elements of a primary and revision system, such as the Genesis II from Smith & Nephew or other total knee system. This allows a surgeon to intra-operatively convert from a primary or revision implant to a hinged implant with common bone cuts and the same instrumentation rather than utilizing a separate system and instruments. The prosthetic system according to one embodiment requires only three additional cuts than are required in a typical revision knee replacement procedure. The extra cuts are needed to accommodate the wider central housing of the femoral component used in the present invention, change the tibial plateau to a neutral (0°) slope, and accommodate the axle. Even with these few additional cuts, the system according to this invention provides relatively simple intra-operative conversion from a standard revision knee to a hinged knee. The prosthetic system according to one embodiment utilizes a pre-assembled femoral component, so that the surgeon does not have to assemble a femoral component based on the tibial insert. The tibial plateau of the present invention can accommodate several thicknesses of tibial inserts enabling the surgeon to choose a tibial insert of appropriate thickness and corresponding cap and use a pre-assembled femoral component. Allowing conversion to the hinge knee of the present invention intra-operatively reduces the risk to the patient by reducing the procedure time.

The prosthetic system according to one embodiment is designed to accept body segments to replace the entire bone in the area of the knee (femur or tibia) in the case of tumor resections or trauma. Such body segments may be secured to the Morse tapers on stem portions 204 and/or 112 in a generally conventional manner or by any other attachment means known in the art. If an additional prosthesis is required for replacement of bone, it is provided as a separate component.

In general, an implant is unstable for several weeks after surgery because there is no scar tissue in the joint envelope. During this time, which typically lasts approximately six weeks but can vary considerably from one patient to the next, it is desirable to not allow rotation along the superior-inferior axis. In an embodiment of the prosthetic system, a bioresorbable bumper 600 (shown in FIG. 5) is placed in the gap of the tibial insert 300 in between the notch 308 and the stop 212 of tibial plateau. This allows an implant to be fixed when implanted, but later allows the implant to rotate as the material is resorbed by the body. The rate of resorption can be selected by choosing the correct composition for bumper 600 to meet the particular needs of the patient.

One embodiment according to this invention is a prosthetic system and kit of parts for replacement of joints, such as a knee. Along with the components described above, the kit of parts includes cutting blocks, reamers, and trials.

One method of using the prosthetic system according to this invention for replacing a joint, such as a knee, is as follows:

(1) resect the proximal end of the tibia to expose the tibial intramedullary canal of the tibia;

(2) resect the distal end of the femur to expose the femoral intramedullary canal;

(3) connect the tibial stem and the femoral stem to the prosthetic system;

(4) insert a femoral stem into the femoral intramedullary canal; and (5) insert a tibial stem into the tibial intramedullary canal. This method additionally includes selecting the appropriate tibial insert and cap intra-operatively.

In an alternative embodiment, the mechanical linkage component can be used in other joints allowing the axis of rotation of the joint to translate in order to provide controlled roll-back and natural kinematics during flexion or extension of the joint.

The disclosure of systems and processes as recited above is not intended to limit the scope of the present invention. Various linking mechanisms can be used that allow the center of contact between the condyles and the tibial insert to move posteriorly during flexion, provide for the movement of the axis of extension-flexion rotation in the superior-inferior direction, allow and control rotation about the superior-inferior axis, and offset the axis of rotation from the superior-inferior axis in order to provide the natural kinematics of the knee joint or other joint.

What is claimed is:

1. A knee prosthesis comprising:
a tibial component having a superior side and an inferior side;
a post configured to project from the superior side of the tibial component;
a femoral component having a pair of condyles; and
a mechanical linkage configured to connect the tibial component and the femoral component, wherein the mechanical linkage defines a flexion-extension axis about which the femoral component can rotate with respect to the tibial component;
wherein the mechanical linkage comprises a link having (i) a posterior portion for coupling to the femoral component and (ii) an anterior portion that defines an aperture configured to receive the post, the anterior portion having a superior edge that defines a boundary of the aperture, wherein the flexion-extension axis is located inferior to the superior edge of the anterior portion of the link.

2. The knee prosthesis of claim 1, wherein the mechanical linkage comprises an axle, and the posterior portion of the link is configured to connect to the axle.

3. The knee prosthesis of claim 1, wherein the mechanical linkage comprises an axle, and wherein the posterior portion of the link has a posterior aperture to receive the axle.

4. The knee prosthesis of claim 3, wherein the post is configured to be fixed to the tibial component, and the link is configured to travel superiorly and inferiorly along the post while the post is fixed to the tibial component.

5. The knee prosthesis of claim 4, wherein the knee prosthesis comprises a feature located at a superior end of the post, wherein the anterior portion of the link is configured to engage the feature to limit superior movement of the femoral component with respect to the tibial component.

6. The knee prosthesis of claim 1, wherein the link is a unitary component that (i) defines a posterior aperture along a medial-lateral axis and (ii) defines the aperture in the anterior portion of the link along a superior-inferior axis.

7. The knee prosthesis of claim 1, wherein the aperture in the anterior portion of the link has a diameter at a superior end of the anterior portion of the link,
wherein the knee prosthesis further comprises a cap configured to mount on the post, the cap having a lip portion that extends beyond a diameter of a superior end of the post and beyond the diameter of the superior end of the aperture in the anterior portion of the link, and
wherein the lip portion is configured to engage the superior end of the anterior portion of the link to prevent distraction of the knee prosthesis.

8. The knee prosthesis of claim 1, wherein the link is configured to travel in a superior-inferior direction along the post during flexion and extension of the knee prosthesis,
wherein the knee prosthesis has a flexion/extension range from extension to a maximum amount of flexion, and
wherein the link is configured to maintain the flexion-extension axis inferior to the superior edge of the anterior portion of the link over the entire flexion/extension range of the knee prosthesis.

9. The knee prosthesis of claim 1, wherein the anterior portion of the link has a superior surface configured to extend around the post when the post is received in the aperture in the anterior portion, and
wherein the posterior portion of the link defines a posterior aperture having a central axis located inferior to the superior surface of the anterior portion.

10. The knee prosthesis of claim 9, wherein the flexion-extension axis of the knee prosthesis is an axis of an axle configured to extend through the posterior aperture.

11. The knee prosthesis of claim 9, wherein a superior surface is substantially perpendicular to a superior-inferior axis.

12. The knee prosthesis of claim 1, further comprising a tibial insert having an aperture, the tibial insert being configured to be positioned on the superior side of the tibial component with the post received in the aperture of the tibial insert.

13. The knee prosthesis of claim 12, wherein the tibial insert is configured to rotate about the post when the post is received in the aperture of the tibial insert.

14. The knee prosthesis of claim 12, wherein the link is configured to rotate about the post during internal-external rotation of the femoral component with respect to the tibial component.

15. The knee prosthesis of claim 1, wherein the superior edge extends around the entire aperture in the anterior portion of the link.

16. A knee prosthesis comprising:
a tibial component having a superior side and an inferior side;
a post configured to project from the superior side of the tibial component;
a femoral component having a pair of condyles; and
a mechanical linkage configured to connect the tibial component and the femoral component, the mechanical linkage comprising an axle configured to extend between the condyles of the femoral component, wherein the mechanical linkage defines a flexion-extension axis through the axle about which the femoral component can rotate with respect to the tibial component;
wherein the mechanical linkage comprises a link having (i) a posterior portion that defines an aperture configured to receive the axle and (ii) an anterior portion that defines an aperture configured to receive the post, the anterior portion having a superior edge that defines a boundary of the aperture, wherein the flexion-extension axis is located inferior to the superior edge of the anterior portion of the link, and the link is configured to maintain the flexion-extension axis inferior to the superior edge of the anterior portion of the link during flexion and extension of the knee prosthesis.

17. The knee prosthesis of claim 16, wherein the mechanical linkage permits the axle to move superiorly and inferiorly.

18. The knee prosthesis of claim 17, wherein the mechanical linkage is configured to constrain superior movement of the axle.

19. The knee prosthesis of claim 17, wherein the mechanical linkage is configured such that the axle moves inferiorly as a flexion angle of the knee prosthesis increases.

20. The knee prosthesis of claim 16, wherein the knee prosthesis is configured to permit internal-external rotation of the femoral component relative to the tibial component.

21. A knee prosthesis comprising:
a tibial component having a superior side and an inferior side;
a post configured to project from the superior side of the tibial component;
a tibial insert configured to be positioned on the superior side of the tibial component, the tibial insert being configured to rotate about the post;
a femoral component having a pair of condyles; and
a mechanical linkage configured to connect the tibial component and the femoral component, the mechanical linkage comprising an axle configured to extend between the condyles of the femoral component, wherein the mechanical linkage defines a flexion-extension axis through the axle about which the femoral component can rotate with respect to the tibial component, wherein the mechanical linkage is configured to rotate about the post and permit internal-external rotation of the femoral component relative to the tibial component;
wherein the mechanical linkage comprises a link having (i) a posterior portion that defines an aperture configured to receive the axle and (ii) an anterior portion that defines an aperture configured to receive the post, the anterior portion having a superior edge that defines a boundary of the aperture, wherein the flexion-extension axis is located inferior to the superior edge of the anterior portion of the link.

* * * * *

UNITED STATES PATENT AND TRADEMARK OFFICE
CERTIFICATE OF CORRECTION

PATENT NO. : 9,693,868 B2
APPLICATION NO. : 15/185701
DATED : July 4, 2017
INVENTOR(S) : Paul Charles Crabtree, Jr. et al.

It is certified that error appears in the above-identified patent and that said Letters Patent is hereby corrected as shown below:

On the Title Page

Item [57], Line 11, after "condyles," delete "an", therefor.

Page 3, Column 1, item [56], under "Other Publications", delete "Endoprothesis" and insert -- Endoprosthesis --, therefor.

Page 3, Column 1, item [56], under "Other Publications", delete "Photopgrah" and insert -- Photograph --, therefor.

Page 3, Column 2, item [56], under "Other Publications", delete "Internaitonal" and insert -- International --, therefor.

In the Specification

Column 1, Line 6, delete "is a is a" and insert -- is a --, therefor.

In the Claims

Column 10, Line 34, Claim 11, after "wherein" delete "a" and insert -- the --, therefor.

Signed and Sealed this
Ninth Day of July, 2019

Andrei Iancu
*Director of the United States Patent and Trademark Office*